United States Patent [19]
Cordier

[11] 4,340,759
[45] Jul. 20, 1982

[54] PROCESS FOR THE PREPARATION OF ANILINES SUBSTITUTED BY CHLORINE IN THE META-POSITION

[75] Inventor: Georges Cordier, Francheville, France

[73] Assignee: Rhone-Poulenc Agrochimie, Lyons, France

[21] Appl. No.: 115,137

[22] Filed: Jan. 24, 1980

[30] Foreign Application Priority Data

Feb. 15, 1979 [FR] France .................................. 79 04482

[51] Int. Cl.$^3$ .............................................. C07C 85/24
[52] U.S. Cl. .................................... 564/412; 564/309; 564/315; 564/330; 564/417
[58] Field of Search ............... 260/570 R, 570 D, 578, 260/580; 564/412, 417, 315, 330, 309

[56] References Cited

U.S. PATENT DOCUMENTS 3,666,813  5/1972  Hindin et al. ...................... 260/580
3,888,929  6/1975  Rivier .............................. 260/580 X
4,085,141  4/1978  Wedemeyer et al. ............... 260/570

Primary Examiner—Robert V. Hines
Attorney, Agent, or Firm—Browdy and Neimark

[57] ABSTRACT

A process for the dechlorination of aromatic nitro or amino compounds consists in reacting anilines or nitrobenzenes which are polysubstituted by chlorine, with hydrogen, under the action of heat, in the presence of cations (Bi, Pb, Sn, Tl, Hg and Ag), in the liquid phase and at low pressure.

The process makes it possible selectively to obtain anilines which are chlorine-substituted in the meta-position.

22 Claims, No Drawings

PROCESS FOR THE PREPARATION OF ANILINES SUBSTITUTED BY CHLORINE IN THE META-POSITION

FIELD OF THE INVENTION

The present invention relates to a process for the preparation of anilines substituted by chlorine in the meta-position, by reacting hydrogen with nitrogen-containing aromatic compounds which are more highly halogen-substituted.

BACKGROUND OF THE INVENTION

U.S. Pat. No. 4,085,141 describes the preparation of chloroanilines substituted in the meta-position, by reacting polychloroanilines with hydrogen. However, the process described in the said patent requires the use of high pressures and of very large amounts of hydrochloric acid, and this presents serious corrosion problems.

SUMMARY OF THE INVENTION

One object of the invention is to provide a process which makes it possible to prepare anilines substituted in the meta-position by chlorine, with good yields, from nitrogen-containing aromatic compounds which are more highly halogen-substituted.

A further object of the invention is to provide a process for the preparation of anilines substituted in the meta-position by chlorine, it being possible for this process to use either chlorine-substituted nitro compounds (substituted nitrobenzenes and the like) or chlorine-substituted amino compounds (polychloroanilines and the like) as the starting reactant.

A further object of the invention is to provide a process for the preparation of anilines substituted in the meta-position by chlorine, using moderate pressures.

A further object of the invention is to provide a process for the preparation of anilines substituted in the meta-position by chlorine, using moderate reaction temperatures.

Yet another object of the invention is to provide a process for the preparation of anilines substituted in the meta-position by chlorine, using moderately corrosive conditions.

Further objects and advantages of the invention will become apparent in the course of the description which now follows.

DETAILED DESCRIPTION OF EMBODIMENTS

It has now been found that these objects can be achieved by virtue of a process for the preparation of anilines substituted in the meta-position by chlorine, which process consists in carrying out the catalytic hydrogenation of chlorine-substituted nitrogen-containing benzene derivatives, in the liquid phase, in an acid medium, under the action of heat, under pressure and in the presence of noble metals from group VIII of the periodic classification, and in which process the benzene derivatives have the formula

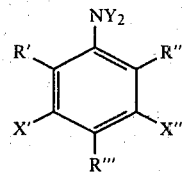

in which: Y represents the hydrogen atom or the oxygen atom, X' and X", which are identical or different from one another, each represent a chlorine atom or an optionally substituted alkyl, aryl, aralkyl, alkoxy or aralkoxy radical, it being furthermore possible for one of the symbols X' and X" to be a hydrogen atom (when preparing monochloroanilines (meta-chloroanilines), only one of the substituents X' or X" represents the chlorine atom, and when preparing dichloroanilines (disubstituted by chlorine in the meta-position), both of the symbols X' and X" represent the chlorine atom), and R', R" and R''', which are identical or different from one another, each represent a chlorine atom or an optionally substituted alkyl, aralkyl, alkoxy or aryloxy radical, at least one of these three symbols representing the chlorine atom and it being furthermore possible for at most two of the symbols R', R" or R''' to be hydrogen, and the reaction is carried out in the presence of heavy metal cations, the heavy metal cations used belonging, in practice, to one of columns 1b to 5a of the periodic classification of the elements (numbering of the columns in accordance with the 1964 edition of "Handbook of Chemistry and Physics", page B-2).

As already stated, the reaction is carried out in the liquid phase; in practice, it is advantageously carried out in the presence of an inorganic or organic solvent which is liquid and inert under the operating conditions. The term inert solvent is understood as meaning a solvent which does not undergo chemical reaction. In fact, the use of water is preferred.

The acidity of the reaction medium is generally such that the pH (in the case of an aqueous medium) is advantageously less than 1.5 and preferably less than 1. The concentration of H+ ions in the medium is generally between 0.5 and 12 g.ions/liter and preferably between 1 and 6 g.ions of H+/liter. The highest concentrations of acid can be used but no significant advantage is gained.

The acidity of the reaction medium can be achieved by means of strong mineral acids, such as sulphuric, phosphoric or hydrogen halide acids, or strong organic acids; however, it is preferred to use hydrogen halide acids and more especially hydrochloric acid. In any case, in view of the presence of chloride ions originating from the dehalogenation, the reaction is in fact carried out, at least in part, in the presence of hydrochloric acid.

The process according to the invention is carried out in the liquid phase (with the exception, of course, of the catalyst based on a noble metal, which most commonly constitutes a solid phase). The liquid phase can by homogeneous and constitute a solution; this is a preferred procedure, in particular in the case where Y is an oxygen atom in the formula (I); a liquid phase of this type therefore contains the reactants, the reaction products and the solvent or solvents which may be present. It is also possible to carry out the reaction with two liquid phases.

The pressure at which the reaction is carried out is generally more than 3 bars (relative pressure) and preferably more than 5 bars. There is not critical upper limit for the pressure, but, for economic reasons, it is generally advantageous to operate at pressures of less than 100 bars, pressures of less than 30 bars being preferred.

The reaction temperature is generally between 90° and 300° C. and preferably between 110° and 200° C. In the case where relatively volatile acids are used, an elevated temperature can lead to a relatively high partial pressure of the compounds, other than hydrogen, in the vapour phase (the term vapour phase is obviously understood as meaning the vapour phase above the liquid reaction medium). The operating conditions are generally chosen so that the hydrogen partial pressure is between 10 and 80% of the total pressure (relative pressure) and preferably between 30 and 60%.

The noble metals constituting the base of the catalysts used in the invention are mainly metals from group VIII of the periodic classification, such as ruthenium, rhodium, palladium, osmium, iridium and platinum; palladium is the preferred metal. The metal can be in the metallic form or in the form of a chemical compound; in general, the metal is preferably employed in the metallic form because, under the operating conditions, the compounds tend to be reduced to the metallic form (oxidation state=zero). The catalyst can be supported or unsupported. Any support which is in itself known for supporting catalysts can be used as the catalyst support, provided that this support is resistant to water and acids; activated carbon, silica and barium sulphate may be mentioned as being more particularly suitable as supports; activited carbon is a preferred support. Both the catalyst and its support are advantageously in the finely divided form; specific surface areas of more than 100 m$^2$/g are generally very suitable.

The amount of catalyst employed is such that the proportion by weight of noble metal from the catalyst, relative to the compound of the formula (I) to be treated, is generally between 0.05 and 10% and preferably between 0.5 and 5%.

In practice, the heavy metal cations used in the invention act as a catalyst favouring the formation of amines which are chlorine-substituted in the meta-position. It can be said that the process of the invention operates with a dual catalyst system; the first catalyst system has already been described and is based on a noble metal (group VIII of the classification); the second catalyst system is based on heavy metals from the groups 1b to 5a of the periodic classification and its function is to favour the formation of amines which are chlorine-substituted in the meta-position; the preferred cations are those based on bismuth, lead, tin, thallium, mercury and silver; cations of this type which may be mentioned more particularly are $Bi^{+++}$, $Pb^{++}$, $Sn^{++}$, $Sn^{++++}$, $Tl^+$, $Tl^{+++}$, $Hg^+$, $Hg^{++}$ and $Ag^+$. These heavy metal cations can be introduced in the most diverse forms, especially in the form of salts (e.g. halides, sulphates and phosphates), but also in the form of compounds of less salt-like character or compounds which are not salts, such as sulphides and oxides. However, under the very highly reducing operating conditions, these various forms are most commonly converted in situ into the cation having the lowest oxidation state. The amounts of heavy metal cation in the reaction medium are most commonly between 0.00001 and 0.1 g.a-tom/liter and preferably between 0.001 and 0.05 g.a-tom/liter. The result of using small amounts of these heavy metal cations is that it is generally unnecessary to recover them at the end of the reaction, except in the case of pollution hazards.

The following may preferably be mentioned as compounds of the formula (I) which can be treated by the process of the invention: 2,3-dichloronitrobenzene and 2,3-dichloroaniline, 2,5-dichloronitrobenzene and 2,5-dichloroaniline, 3,4-dichloronitrobenzene and 3,4-dichloroaniline, 2,3,4-trichloronitrobenzene and 2,3,4-trichloroaniline, 2,3,5-trichloronitrobenzene and 2,3,5-trichloroaniline, 2,3,6-trichloronitrobenzene and 2,3,6-trichloroaniline, 2,4,5-trichloronitrobenzene and 2,4,5-trichloroaniline, 3,4,5-trichloronitrobenzene and 3,4,5-trichloroaniline, 2,3,4,6-tetrachloronitrobenzene and 2,3,4,6-tetrachloroaniline, 2,3,4,5-tetrachloronitrobenzene and 2,3,4,5-tetrachloroaniline, 2,3,5,6-tetrachloronitrobenzene and 2,3,5,6-tetrachloroaniline, and pentachloronitrobenzene and pentachloroaniline, but also 4,5,6-trichloro-2-methylnitrobenzene and 4,5,6-trichloro-2-methylaniline, 2,5-dichloro-4-methylnitrobenzene and 2,5-dichloro-4-methylaniline, 2,3,5,6-tetrachloro-4-methylnitrobenzene and 2,3,5,6-tetrachloro-4-methylaniline, 2,5-dichloro-3,4-dimethylnitrobenzene and 2,5-dichloro-3,4-dimethylaniline, 2,5-dichloro-4-ethylnitrobenzene and 2,5-dichloro-4-ethylaniline, 2,5-dichloro-4-propylnitrobenzene and 2,5-dichloro-4-propylaniline, 3,4,6-trichloro-2-benzylnitrobenzene and 3,4,6-trichloro-2-benzylaniline, 2,2'-dinitro-3,5,6,3',5',6'-hexachlorodiphenylmethane and 2,2'-diamino-3,5,6,3',5',6'-hexachlorodiphenylmethane, 2-nitro-3,4,5-trichlorodiphenyl and 2-amino-3,4,5-trichlorodiphenyl, 4,4'-dinitrooctachlorodiphenyl and 4,4'-diaminooctachlorodiphenyl, 4,5-dichloro-2-methoxynitrobenzene and 4,5-dichloro-2-methoxyaniline, 3,4-dichloro-2-methoxynitrobenzene and 3,4-dichloro-2-methoxyaniline, 3,6-dichloro-2-methoxynitrobenzene and 3,6-dichloro-2-methoxyaniline, 5,6-dichloro-2-methoxynitrobenzene and 5,6-dichloro-2-methoxyaniline, 3,4,6-trichloro-2-methoxynitrobenzene and 3,4,6-trichloro-2-methoxyaniline, 3,4,5-trichloro-2-methoxynitrobenzene and 3,4,5-trichloro-2-methoxyaniline, 3,4,5,6-tetrachloro-2-methoxynitrobenzene and 3,4,5,6-tetrachloro-2-methoxyaniline, 4,5-dichloro-3-methoxynitrobenzene and 4,5-dichloro-3-methoxyaniline, 5,6-dichloro-3-methoxynitrobenzene and 5,6-dichloro-3-methoxyaniline, 2,5-dichloro-3-methoxynitrobenzene and 2,5-dichloro-3-methoxyaniline, 4,5,6-trichloro-3-methoxynitrobenzene and 4,5,6-trichloro-3-methoxyaniline, 2,4,5,6-tetrachloro-3-methoxynitrobenzene and 2,4,5,6-tetrachloro-3-methoxyaniline, 2,3-dichloro-4-methoxynitrobenzene and 2,3-dichloro-4-methoxyaniline, 2,5-dichloro-4-methoxynitrobenzene and 2,5-dichloro-4-methoxyaniline, 2,3,6-trichloro-4-methoxynitrobenzene and 2,3,6-trichloro-4-methoxyaniline, 2,3,5-trichloro-4-methoxynitrobenzene and 2,3,5-trichloro-4-methoxyaniline, 2,3,5,6-tetrachloro-4-methoxynitrobenzene and 2,3,5,6-tetrachloro-4-methoxyaniline, 4,5-dichloro-2-phenoxynitrobenzene and 4,5-dichloro-2-phenoxyaniline, 3,4,5,6-tetrachloro-2-phenoxynitrobenzene and 3,4,5,6-tetrachloro-2-phenoxyaniline, 2,4,5,6-tetrachloro-3-phenoxynitrobenzene and 2,4,5,6-tetrachloro-3-phenoxyaniline, 2,5-dichloro-4-phenoxynitrobenzene and 2,5-dichloro-4-phenoxyaniline, and 2,3,5,6-tetrachloro-4-phenoxynitrobenzene and 2,3,5,6-tetrachloro-4-phenoxyaniline.

The following may preferably be mentioned amongst the anilines which are substituted in the meta-position by a chlorine atom and which can be prepared by the process according to the invention: meta-chloroaniline and 3,5-dichloroaniline, but also: 5-chloro-2-methylaniline, 5-chloro-3-methylaniline, 3-chloro-4-methylaniline, 3,5-dichloro-4-methylaniline, 5-chloro-3,4-dimethylaniline, 3-chloro-4-ethylaniline, 3-chloro-2-benzylaniline, 4,4'-diamino-2,6,2',6'-tetrachlorodiphenyl, 3-chloro-2methoxyaniline, 5-chloro-2-methoxyaniline, 3,5-dichloro-2-methoxyaniline, 3-chloro-4-methoxyaniline, 5-chloro-3-methoxyaniline, 3,5-dichloro-4-methoxyaniline, 3-chloro-2-phenoxyaniline, 5-chloro-2-phenoxyaniline, 3,5-dichloro-2-phenoxyaniline and 3,5-dichloro-4-phenoxyaniline.

The process according to the invention can be carried out continuously or discontinuously. At the end of the reaction, the catalyst can be separated off, if necessary, by filtration or by equivalent means such as draining; the amine prepared, which is chlorine-substituted in the meta-position, can be separated off by any means which is in itself known, e.g. by solvent extraction and/or by distillation; before carrying out this separation, it is generally appropriate to convert the amine (salified in an acid medium) back into the form of an (unsalified) amine by rendering the reaction mixture neutral or alkaline with the aid of an alkaline agent.

The process according to the invention is very advantageous because of its good selectivity with respect to the amine which is chlorine-substituted in the meta-position, and because of the relatively mild conditions under which it can be carried out. The amines produced in this way, which are chlorine-substituted in the meta-position, can be used, in particular, for manufacturing pesticides.

The examples, which are given without implying a limitation, illustrate the invention and show how it can be put into effect.

EXAMPLES 1 TO 6

2,3,4,5-Tetrachloroaniline (0.416 g), a catalyst consisting of palladium deposited on carbon black (specific surface area of the activited carbon: 1,100 m²/g; proportion of palladium by weight: 10%)(0.14 g), an aqueous solution of hydrochloric acid having a concentration of 4 mols/liter (120 cc) and a metal salt, in an amount which is such that the concentration in g.atom/-liter of the metal in question (in the form of a cation) is that given in Table I, are introduced into a 250 cc autoclave coated on the inside with tantalum.

The autoclave is closed and purged first with argon and then with hydrogen. The temperature is then raised to 160° C., whilst allowing the autogenous pressure to increase, and then, when this temperature has been reached, hydrogen is introduced until the total (relative) pressure is 13 bars, the hydrogen partial pressure being 6 bars.

The reaction is allowed to proceed under these conditions for the reaction time indicated in Table I. After cooling, the liquid reaction mixture is rendered alkaline with an aqueous solution of sodium hydroxide (NaOH); the catalyst is filtered off; the 3,5-dichloroaniline is extracted from the aqueous phase using methylene chloride; the methylene chloride solution thus obtained is dried over sodium sulphate; the solvent is evaporated off in vacuo. In the various examples, the degree of conversion of the tetrachloroaniline was 100%. The yield of 3,5-dichloroaniline obtained for each of the examples is indicated in Table I.

TABLE I

| Example | Metal salt Nature | Concentration of the cation in g.atom/liter | Reaction time | Yield in % |
|---|---|---|---|---|
| 1 | TlCl | 0.005 | 2 hours 20 minutes | 96.8 |
| 2 | PbSO$_4$ | 0.05 | 2 hours 30 minutes | 95.7 |
| 3 | SnCl$_2$ | 0.005 | 3 hours | 92.7 |
| 4 | BiCl$_3$ | 0.005 | 3 hours 30 minutes | 98.4 |
| 5 | Ag$_2$SO$_4$ | 0.005 | 3 hours 55 minutes | 98.1 |
| 6 | HgCl$_2$ | 0.001 | 7 hours 30 minutes | 97.8 |

I claim:

1. A process for the preparation of anilines substituted in the meta-position by chlorine, by the catalytic hydrogenation of chlorine-substituted nitrogen-containing benzene derivatives, in the liquid phase, in an acid medium, under the action of heat, under pressure and in the presence of noble metals from group VIII of the periodic classification, in which process the benzene derivatives have the formula:

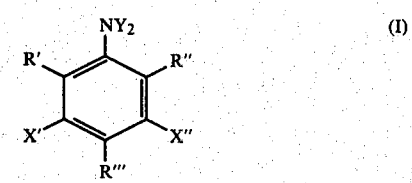

in which Y represents the hydrogen atom or the oxygen atom, X' and X", which are identical or different from one another, each represent a chlorine atom or an optionally substituted alkyl, aryl, aralkyl, alkoxy or aralkoxy radical, or one of X' and X" is hydrogen, and R', R" and R''', which are identical or different from one another, each represent a chlorine atom or an optionally substituted alkyl, aralkyl, alkoxy or aryloxy radical, at least one of these three representing the chlorine atom and at most two of R', R" or R''' being hydrogen, and the reaction is carried out in the presence of heavy metal cations belonging to one of columns 1b to 5a of the periodic classification.

2. A process according to claim 1, in which the metal cation is derived from bismuth, lead, tin, thallium, mercury or silver.

3. A process according to claim 2, in which the metal cation is one of the cations Bi$^{+++}$, Pb$^{++}$, Sn$^{++}$, Sn$^{++++}$, Tl$^+$, Tl$^{+++}$, Hg$^+$, Hg$^{++}$ and Ag$^+$.

4. A process according to claim 1, in which the concentration of heavy metal cation is between 0.00001 and 0.1 g.atom/liter.

5. A process according to claim 4, in which R', R", R''', X' and X", which are identical or different from one another, represent the hydrogen atom or the chlorine atom.

6. A process for the preparation of optionally substituted meta-dichloroanilines, according to claim 5, in which X' and X" represent the chlorine atom.

7. A process for the preparation of optionally substituted meta-monochloroanilines, according to claim 1, in which only one of the two radicals X' and X" is the chlorine atom.

8. A process for the preparation of 3,5-dichloroaniline, according to claim 5, in which Y is the hydrogen or oxygen atom, X' and X" are the chlorine atom and R', R" and R'" are the hydrogen atom or the chlorine atom, at least one of them being the chlorine atom.

9. A process according to claim 8, in which the pH is less than 1.5 and/or the concentration of $H^+$ ions in the reaction medium is between 0.5 and 12 g.ions/liter.

10. A process according to claim 9, in which the pH is less than 1 and/or the concentration of $H^+$ ions in the reaction medium is between 1 and 6 g.ions/liter.

11. A process according to claim 9, in which the reaction medium is an aqueous medium.

12. A process according to claim 11, in which the reaction medium consists only of a liquid phase, except for the catalyst based on a noble metal.

13. A process according to claim 12, in which the total pressure is between 3 and 100 bars.

14. A process according to claim 13, in which the total pressure is between 5 and 30 bars.

15. A process according to claim 13, in which the temperature is between 90° and 300° C.

16. A process according to claim 1, in which the hydrogen partial pressure is between 10 and 80% of the total pressure.

17. A process according to claim 16, in which the hydrogen partial pressure is between 30 and 60% of the total pressure.

18. A process according to claim 1, in which the noble metal catalyst is palladium.

19. A process according to claim 1, in which the proportion by weight of noble metal, relative to the compound of the formula (I), is between 0.05 and 10%.

20. A process according to claim 3, wherein the concentration of heavy metal cation is between 0.001 and 0.05 g.atom/liter.

21. A process according to claim 3, in which the temperature is between 110° and 200° C.

22. A process according to claim 3, in which the proportion by weight of noble metal catalyst, relative to the compound of formula (I), is between 0.5 and 5%.

* * * * *